(12) United States Patent
Gupta et al.

(10) Patent No.: US 7,732,205 B2
(45) Date of Patent: Jun. 8, 2010

(54) DEVELOPMENT AND STRATIFICATION OF PINE SOMATIC EMBRYOS USING A LIQUID SYSTEM

(75) Inventors: Pramod K. Gupta, Federal Way, WA (US); Diane G. Holmstrom, Sumner, WA (US); Bonnie Larson, Granite Falls, WA (US); Judith Zucati, Maple Valley, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 1237 days.

(21) Appl. No.: 10/875,656

(22) Filed: Jun. 24, 2004

(65) Prior Publication Data

US 2005/0026281 A1 Feb. 3, 2005

Related U.S. Application Data

(60) Provisional application No. 60/491,388, filed on Jul. 30, 2003.

(51) Int. Cl.
*C12N 5/00* (2006.01)
*C12N 5/02* (2006.01)
*A01H 11/00* (2006.01)
*A01H 9/00* (2006.01)
*A01H 5/00* (2006.01)

(52) U.S. Cl. ............. 435/422; 435/420; 435/430.1; 435/410; 800/295; 800/298

(58) Field of Classification Search ............. 435/422, 435/420
See application file for complete search history.

(56) References Cited

U.S. PATENT DOCUMENTS

| | | | |
|---|---|---|---|
| 4,217,730 A | 8/1980 | Abo El-Nil | |
| 4,615,141 A * | 10/1986 | Janick et al. ............. | 47/57.6 |
| 4,801,545 A | 1/1989 | Stuart et al. | |
| 4,957,866 A | 9/1990 | Gupta et al. | |
| 5,034,326 A | 7/1991 | Pullman et al. | |
| 5,036,007 A | 7/1991 | Gupta et al. | |
| 5,041,382 A | 8/1991 | Gupta et al. | |
| 5,183,757 A | 2/1993 | Roberts | |
| 5,187,092 A | 2/1993 | Uddin | |
| 5,236,841 A | 8/1993 | Gupta et al. | |
| 5,238,835 A | 8/1993 | McKersie et al. | |
| 5,294,549 A | 3/1994 | Pullman et al. | |
| 5,413,930 A | 5/1995 | Becwar et al. | |
| 5,464,769 A | 11/1995 | Attree et al. | |
| 5,482,857 A | 1/1996 | Gupta et al. | |
| 5,491,090 A | 2/1996 | Handley, III et al. | |
| 5,501,972 A | 3/1996 | Westcott | |
| 5,506,136 A | 4/1996 | Becwar et al. | |
| 5,523,230 A | 6/1996 | Smith | |
| 5,534,433 A | 7/1996 | Coke | |
| 5,534,434 A | 7/1996 | Coke | |
| 5,563,061 A * | 10/1996 | Gupta .................. | 435/422 |
| 5,564,224 A | 10/1996 | Carlson et al. | |
| 5,565,355 A | 10/1996 | Smith | |
| 5,587,312 A | 12/1996 | van Holst et al. | |
| 5,610,051 A | 3/1997 | Becwar et al. | |
| 5,677,185 A | 10/1997 | Handley, III | |
| 5,731,191 A | 3/1998 | Rutter et al. | |
| 5,731,203 A | 3/1998 | Handley, III | |
| 5,731,204 A * | 3/1998 | Rutter et al. ............. | 435/430.1 |
| 5,821,126 A | 10/1998 | Durzan et al. | |
| 5,840,581 A | 11/1998 | Carraway et al. | |
| 5,850,032 A | 12/1998 | Wann | |
| 5,856,191 A | 1/1999 | Handley, III | |
| 5,985,667 A | 11/1999 | Attree et al. | |
| 6,022,744 A | 2/2000 | Tetteroo et al. | |
| 6,117,678 A | 9/2000 | Carpenter et al. | |
| 6,134,830 A | 10/2000 | Welty | |
| 6,150,167 A | 11/2000 | Carpenter et al. | |
| 6,180,405 B1 | 1/2001 | Aitken-Christie et al. | |
| 6,200,809 B1 | 3/2001 | Klimaszewska et al. | |
| 6,340,594 B1 | 1/2002 | Attree et al. | |
| 6,372,496 B1 | 4/2002 | Attree et al. | |
| 6,417,001 B2 | 7/2002 | Aitken-Christie et al. | |
| 6,444,467 B1 | 9/2002 | Fan et al. | |
| 6,492,174 B1 | 12/2002 | Pullman et al. | |
| 2002/0012994 A1 | 1/2002 | Aitken-Christie et al. | |

(Continued)

FOREIGN PATENT DOCUMENTS

EP         0 300 730 B1       1/1989

(Continued)

OTHER PUBLICATIONS

Conger B.V. Critical reviews in Plant Sciences vol. 10 / issue 1 p. 31-61 CRC Press INC.*

(Continued)

*Primary Examiner*—Annette H Para
(74) *Attorney, Agent, or Firm*—Christensen O'Connor Johnson Kindness

(57) ABSTRACT

The invention provides methods for producing pine somatic embryos using a liquid development medium and/or a liquid stratification medium. In a first aspect, the methods comprise the step of culturing embryogenic cells in, or on, a liquid development medium to produce cotyledonary pine somatic embryos. In another aspect, the methods comprise the step of culturing pine cotyledonary somatic embryos in, or on, a liquid stratification medium to produce stratified cotyledonary somatic embryos. The invention also provides methods for producing pine somatic embryos in bioreactors.

20 Claims, No Drawings

U.S. PATENT DOCUMENTS

2002/0092037 A1     7/2002     Connett-Porceddu et al.
2002/0100083 A1     7/2002     Connett-Porceddu et al.

FOREIGN PATENT DOCUMENTS

| | | |
|---|---|---|
| EP | 0 618 766 B1 | 10/1994 |
| EP | 0 934 691 A2 | 8/1999 |
| WO | WO 95/33822 A1 | 12/1995 |
| WO | WO 98/48279 A1 | 10/1998 |
| WO | WO 99/46977 | 9/1999 |
| WO | WO 01/20972 A1 | 9/2000 |

OTHER PUBLICATIONS

Tautorus et al. Nutrient Utilization during Bioreactor Culture and maturation of Somatic Embryo Cultures of Picea Mariana and Picea Glauca-Engelmannii. 1994. In Vitro Cell Dev. Biol. 3OP:58-63. Jan. 1994.*

Gupta PK et al, "Liquid media and automation strategy for large-scale production of conifer somatic embryos for reforestation," *In vitro cell & devel bio-Animal* 1999, 35: Abstract W-32.

Gupta PK et al, "Somatic embryo development in liquid medium for large-scale propagation of conifer trees," *2003 Congress on In Vitro Biol* May 31-Jun. 4, 2003; program abstracts p. 14A, Abstract P-28.

Lin X, "Culture of isolated zygotic embryos of pinus radiata D. Don. Part 1: Factors influencing in vitro germination and growth of isolated embryos," *In Vitro Cell & Develop Biol-Plant*, 38: 2002, pp. 191-197.

Vágner M et al., "Norway spruce somatic embryogenesis: Membrane rafts as compromise between liquid and solidified media," *1$^{st}$ Intl Symp Liq Sys for in vitro Mass Propagation of Plants*, Abstracts, pp. 28-29, 2002.

Ramarosandtradana LH et al, "Effects of Carbohydrate Source, Polyethylene Glycol and Gellan Gum Concentration on Embryonal-Suspensor Mass (ESM) Proliferation and Maturation of Maritime Pine Somatic Embryos," *In vitro Cellular and Developmental Biology-Plant* 37:29-34.

Klimaszewska K et al, "Maturation of somatic embryos of *Pinus strobes* is promoted by a high concentration of gellan gum," *Physiologica Plantarum* (100) 949-957, 1997.

Garin E et al, "Effects of sugars, amino acids, and culture technique on maturation of somatic embryos of *Pinus strobes* on medium with two gellan gum concentrations," *Plant Cell Tiss & Org Cult* (62) 27-27, 2000.

Lelu MA et al, "Somatic embryogenesis and plantlet development in *Pinus sylvestris* and *Pinus pinaster* on median with and without growth regulators," *Phys Plantarum, Munksgaard Intl* (105) 719-718, 1999.

Taber RP et al., "Kinetics of Douglas-fir (*Pseudotsungo menziesii*) somatic embryo development," *Can J Bot* (76): 838-871, 1998.

Attree, S.M. et al., "Somatic Embryo Maturation, Germination, and Soil Establishment of Plants of Black and White Spruce (*Picea mariana* and *Picea glauca*)," Can. J. Bot. 68:2583-2589, 1990.

Boulay, M.P., et al., "Development of Somatic Embryos From Cell Suspension Cultures of Norway Spruce (*Picea abies* Karst.)," Plant Cell Reports 7:134-137, 1988.

Gupta, P.K., et al., "Scale-Up Somatic Embryogenesis of Conifers For Reforestation," Proceedings of the 3rd Canadian Workshop on Plant Tissue Culture and Genetic Engineering, University of Guelph, Symposium 1: Somatic Embryogenesis and Synthetic Seeds, Abstract, Jun. 1992.

Jain, S.M., et al., Forestry Sciences: Somatic Embryogenesis in Woody Plants, vol. 3, Gymnosperms, Kluwer Academic Publishers, Netherlands, 1995.

Keinonen-Mettälä, K., et al., "Somatic Embryogenesis of *Pinus sylvestris*," Scand. J. For. Res. 11:242-250, 1996.

Mathur, G. et al., "Studies on Somatic Embryogenesis From Immature Zygotic Embryos of CHIR Pine (*Pinus roxburghii* Sarg.)," Current Science 79(7):999-1004, 2000.

Timmis, R., "Bioprocessing for Tree Production in the Forest Industry: Conifer Somatic Embryogenesis," Biotechnol. Prog. 14(1):156-166, 1998.

Von Aderkas, P., et al., "Charcoal Affects Early Development and Hormonal Concentrations of Somatic Embryos of Hybrid Larch," Tree Physiology 22:431-434, 2002.

Nagmani, R., et al., "Anatomical Comparison of Somatic and Zygotic Embryogeny in Conifers," in S.M. Jain et al. (eds.), vol. 1, Somatic Embryogenesis in Woody Plants, Series: Forestry Sciences, vol. 44, 1995, pp. 23-48.

* cited by examiner

DEVELOPMENT AND STRATIFICATION OF PINE SOMATIC EMBRYOS USING A LIQUID SYSTEM

CROSS REFERENCE TO RELATED APPLICATION

The present application claims the benefit of U.S. Provisional Application No. 60/491,388, filed Jul. 30, 2003.

FIELD OF THE INVENTION

The present invention relates to methods for producing pine somatic embryos.

BACKGROUND OF THE INVENTION

The demand for coniferous trees, such as pines and firs, to make wood products continues to increase. One proposed solution to this problem is to identify individual trees that possess desirable characteristics, such as a rapid rate of growth, and produce numerous, genetically identical, clones of the superior trees by somatic cloning.

Somatic cloning is the process of creating genetically identical trees from tree tissue other than the male and female gametes. In one approach to somatic cloning, plant tissue is cultured in an initiation medium that includes hormones, such as auxins and/or cytokinins, to initiate formation of embryogenic cells, such as embryonal suspensor masses, that are capable of developing into somatic embryos. The embryogenic cells are then further cultured in a maintenance medium that promotes establishment and multiplication of the embryogenic cells. The multiplied embryogenic cells are then cultured in a development medium that promotes development of somatic embryos which can, for example, be placed within manufactured seeds and sown in the soil where they germinate to yield seedlings. The seedlings can be transplanted to a growth site for subsequent growth and eventual harvesting to yield lumber, or wood-derived products.

The present invention provides methods that are useful for somatic cloning of pine. In particular, the methods of the invention are applicable for the large-scale production of pine somatic embryos.

SUMMARY OF THE INVENTION

The invention provides methods for producing pine somatic embryos using liquid development media and/or liquid stratification media. The methods of the invention are applicable to any member of the genus *Pinus*, such as Loblolly pine (*Pinus taeda*).

In one aspect, the methods comprise the step of culturing embryogenic cells in, or on, a liquid development medium to produce cotyledonary pine somatic embryos. The liquid development medium typically has an osmolality of between about 200 mM/kg to about 600 mM/kg, such as between about 250 mM/kg and about 350 mM/kg. The embryogenic cells may be cultured in liquid development medium or on liquid development medium-soaked pads. The methods of the invention produce a higher yield of cotyledonary embryos of a more consistent quality than otherwise identical methods that do not use a liquid development medium. For example, the methods of the invention produce an about 4-fold to about 10-fold increase in the number of cotyledonary embryos compared to an otherwise identical method using a semi-solid development medium that is equivalent to the liquid development medium. In some embodiments, the cotyledonary embryos produced using the methods of the invention develop faster and are longer than cotyledonary embryos produced using an otherwise identical method using a semi-solid development medium that is equivalent to the liquid development medium. Some embodiments produce a yield of at least about 500 cotyledonary embryos, such as at least about 1000 cotyledonary embryos or at least about 2000 cotyledonary embryos, per 100 mg of embryogenic cells.

The methods may further comprise the step of culturing cotyledonary somatic embryos in, or on, a stratification medium to produce stratified cotyledonary somatic embryos. For example, the embryos may be cultured in, or on, a stratification medium in a bioreactor. The stratification medium may be a liquid medium. Typically, cotyledonary embryos are cultured in, or on, a stratification medium for about 1 to about 6 weeks (such as about 4 weeks) at a temperature from about 1° C. to about 6° C. (such as from about 1° C. to about 4° C.).

In another aspect, the methods comprise the step of culturing pine cotyledonary somatic embryos in, or on, a liquid stratification medium to produce stratified cotyledonary somatic embryos. The cotyledonary embryos may be cultured in liquid stratification medium or on liquid stratification medium-soaked pads. The cotyledonary embryos may be cultured in, or on, a liquid stratification medium for about 1 to about 6 weeks (such as about 4 weeks) at a temperature from about 1° C. to about 6° C. (such as from about 1° C. to about 4° C.). In some embodiments, the step of culturing pine cotyledonary somatic embryos in, or on, a liquid stratification medium produces an increase, such as an about 2-fold to about 4-fold increase, in the germination efficiency of cotyledonary embryos compared to an identical method without the stratification step. Some embodiments of culturing pine cotyledonary somatic embryos on liquid stratification medium produce a similar efficiency of germination as produced by culturing the embryos on a semi-solid stratification medium that is otherwise identical to the liquid stratification medium.

According to the methods of the invention, the embryogenic cells may be cultured in a bioreactor. For example, the embryogenic cells may be cultured in, or on, a liquid development medium in a bioreactor to produce cotyledonary embryos. The bioreactor may be a tray, such as a stainless steel tray or a plastic tray. In some embodiments, at least about 1 g (fresh weight) of embryogenic cells, such as about 2 g or about 10 g of embryogenic cells, are cultured in a bioreactor. In some embodiments, the yield of cotyledonary embryos is similar to the yield obtained using an identical method but without the use of a bioreactor. The cotyledonary embryos may further be cultured in, or on, liquid stratification medium in a bioreactor to produce stratified cotyledonary embryos. In some embodiments, at least about 100 of cotyledonary embryos, such as about 1000 or about 10,000 of cotyledonary, are cultured in a bioreactor. In some embodiments of producing somatic embryos in bioreactors, the methods of the invention provide a germination rate that is similar to the germination rate obtained without the use of a bioreactor but using an otherwise identical method.

DETAILED DESCRIPTION OF THE PREFERRED EMBODIMENT

Unless specifically defined herein, all terms used herein have the same meaning as they would to one skilled in the art of the present invention.

As used herein, the terms "embryogenic cells" refers to any cells, including cells that are organized to form a tissue or an organ, derived from a plant of the genus *Pinus*, that are capable of producing one or more pine somatic embryos when treated in accordance with the methods of the invention. Thus, the term "embryogenic cells" includes, for example, Loblolly pine (*P. taeda*) embryonal suspensor masses (ESMs). As used herein, weight measurements of ESMs are provided as fresh weights of ESMs.

As used herein, the term "cotyledonary embryo" refers to an embryo that possesses at least one cotyledon. The term "pre-cotyledonary embryo" refers to an embryo that does not possess any cotyledons.

Unless stated otherwise, all concentration values that are expressed as percentages are weight per volume percentages.

The present invention provides methods for producing pine somatic embryos using a liquid development medium and/or a liquid stratification medium. The methods of the invention are applicable to any member of the genus *Pinus*, such as Loblolly pine (*Pinus taeda*).

In a first aspect, the methods comprise the step of culturing embryogenic cells in, or on, a liquid development medium to produce cotyledonary pine somatic embryos. Current protocols use a solid or semi-solid development medium for producing cotyledonary embryos, which has several disadvantages. For example, temperature-sensitive components of the medium have to be added within a narrow temperature range and culture plates have to be poured manually. In addition, the semi-solid medium has a limited shelf life. These factors impede large-scale production of embryos. The first aspect of the present invention addresses these problems by culturing the embryonic cells in, or on, a liquid development medium.

Exemplary embryogenic cells that are useful in the practice of the present invention are embryonal suspensor masses (ESMs). ESMs can be prepared, for example, from pre-cotyledonary embryos removed from seed. For example, the seed are surface sterilized before removing the pre-cotyledonary embryos which are then cultured on, or in, an induction medium that promotes formation of ESMs, which include early stage embryos in the process of multiplication by budding and cleavage. A representative example of an induction medium is medium $BM_1$ described in EXAMPLE 1 of the present application.

The liquid development medium typically contains nutrients that sustain the embryogenic tissue. For example, maltose may be included in the medium as the principal or sole source of sugar for the embryogenic tissue. Useful maltose concentrations are within the range of from about 1% to about 2.5%. Maltose may also be included in the medium together with glucose. Useful glucose concentrations are within the range of from about 1% to about 2.5%.

Suitable development media typically do not include growth-promoting hormones, such as auxins and cytokinins, but may include the hormone abscisic acid. Abscisic acid is a sesquiterpenoid plant hormone that is implicated in a variety of plant physiological processes (see, e.g., Milborrow (2001) *J. Exp. Botany* 52:1145-1164; Leung & Giraudat (1998) *Ann. Rev. Plant Physiol. Plant Mol. Biol.* 49: 199-123). In some embodiments of the methods of the invention, the concentration of abscisic acid in the liquid development medium is between 1 mg/l and 200 mg/l, such as between 5 mg/l and 50 mg/l.

The liquid development medium may also include one or more gibberellins. Gibberellins are a class of diterpenoid plant hormones (see, e.g., Krishnamoorthy (1975) Gibberellins and Plant Growth, John Wiley & Sons). Representative examples of gibberellins useful in the practice of the present invention include gibberellic acid, gibberellin 4 and gibberellin 7, which are each disclosed, for example, in the aforementioned Krishnamoorthy text book. An example of a useful mixture of gibberellins is a mixture of gibberellin 4 and gibberellin 7 (referred to as gibberellin 4/7), such as the gibberellin 4/7 sold by Abbott Laboratories, Chicago, Ill. In some embodiments of the methods of the invention, the concentration of gibberellin(s) in the liquid development medium is between 0.5 mg/l and 500 mg/l, such as between 1 mg/l and 100 mg/l or between 5 mg/l and 50 mg/l. In those embodiments of the methods of the invention in which more than one gibberellin is present in the liquid development medium, the foregoing concentration ranges refer to the total gibberellin concentration in the synchronization medium.

The liquid development medium may also include an adsorbent composition. Non-limiting examples of useful adsorbent compositions include activated charcoal, soluble poly(vinyl pyrrolidone), insoluble poly(vinyl pyrrolidone), activated alumina, and silica gel. The adsorbent composition may be present in an amount, for example, from 0.1 g/l to 50 g/L. In some embodiments, the adsorbent composition is present in an amount of from 0.5 g/l to 5 g/l, or from about 0.5 g/l to about 1.0 g/l. In those embodiments of the methods of the invention in which more than one adsorbent composition is present in the liquid development medium, the foregoing concentration ranges refer to the total adsorbent composition concentration in the medium.

The osmolality of the development medium may be adjusted to a value that falls within a desired range, such as from about 250 mM/Kg to about 450 mM/Kg. In some embodiments, the osmolality of the liquid development medium is between about 250 mM/kg and 300 mM/kg or between about 350 mM and about 400 mM. Examples of suitable liquid development media include medium $BM_5$, set forth in EXAMPLE 1 herein, $BM_8$, set forth in EXAMPLE 2 herein, and $BM_{10}$, set forth in EXAMPLE 6 herein.

The embryogenic cells may be cultured in, or on, the liquid development medium. Accordingly, the embryogenic cells may be cultured in liquid development medium by completely immersing them in liquid development medium and, optionally, agitating them, as described in EXAMPLE 6. The embryogenic cells may also be cultured on the surface of a liquid development medium of a suitable density to allow the embryogenic cells to float. In addition, the embryogenic cells may be cultured on liquid development by placing them on pads soaked with liquid medium, as described in EXAMPLES 1, 2, 4, and 5. Any type of pads may be used. Typically, the pore size of the pad is between 10 and 1000 micrometers. Suitable pads include cellulose pads, filter papers, polyester pads, and foam pads. Optionally, more than one pad may be used. For example, embryogenic cells such as ESMs may be transferred to filter paper on top of development medium-soaked cellulose pads, as described in EXAMPLES 1 and 5.

In some embodiments, the embryogenic cells are cultured in, or on, liquid development medium in a bioreactor. For example, the embryogenic cells may be cultured in liquid development medium, or on liquid development medium-soaked pads in a bioreactor, as described in EXAMPLE 5. A bioreactor is a sealed or sealable container that provides a sterile environment in which a multiplicity of embryogenic cells may be cultured. For example, a bioreactor may be an autoclavable container that is large enough to contain at least about 2 to 10 liters of medium. Suitable bioreactors include, but are not limited to, stainless steel trays or plastic Cambro trays, as described in EXAMPLE 5. In some embodiments, at least about 1 g of embryogenic cells, such as about 2 g or about 10 g of embryogenic cells, are cultured in a bioreactor.

Pine embryogenic cells may be cultured in, or on, a liquid development medium for a period of from 9 weeks to 14 weeks, such as from 10 weeks to 12 weeks, or such as about 12 weeks, at a temperature of from 10° C. to 30° C., such as from 15° C. to 25° C., or such as from 20° C. to 23° C.

In some embodiments, the methods of the first aspect of the invention comprise the steps of: (a) culturing pine somatic cells in, or on, an induction medium to produce embryogenic cells; (b) culturing the embryogenic cells prepared in step (a) in, or on, a maintenance medium to multiply the embryogenic cells; and (c) culturing the embryogenic cells multiplied in step (b) in, or on, a liquid development medium to produce cotyledonary somatic embryos.

In the first step pine somatic cells are cultured in, or on, an induction medium. The induction medium generally includes inorganic salts and organic nutrient materials. For example, the induction medium may include maltose as a carbohydrate source. Examples of useful maltose concentrations are within the range from about 1% to about 5%, such as about 3%. The osmolality of the induction medium is typically about 160 mM/kg or even lower, but it may be as high as 170 mM/kg. The induction medium typically includes growth hormones. Examples of hormones that can be included in the induction medium are auxins (e.g., 2,4-dichlorophenoxyacetic, acid (2,4-D)) and cytokinins (e.g., 6-benzylaminopurine (BAP)). Auxins can be utilized, for example, at a concentration of from 1 mg/l to 200 mg/l. Cytokinins can be utilized, for example, at a concentration of from 0.1 mg/l to 10 mg/l.

The induction medium may contain an adsorbent composition, especially when very high levels of growth hormones are used. The adsorbent composition can be any composition that is not toxic to the embryogenic cells at the concentrations utilized in the practice of the present methods, and that is capable of absorbing growth-promoting hormones, and toxic compounds produced by the plant cells, that are present in the medium. Examples of useful adsorbent compositions are described above. The adsorbent composition may be present in an amount, for example, from about 0.1 g/l to about 5 g/l. An example of an induction medium useful in the practice of the present invention is medium $BM_1$, set forth in EXAMPLE 1 herein.

Pine somatic cells are typically cultured in, or on, an induction medium for a period of from 6 weeks to 12 weeks, such as from 8 weeks to 10 weeks, or such as about 8 weeks, at a temperature of from 10° C. to 30° C., such as from 15° C. to 25° C., or such as from 20° C. to 23° C.

In the second step, the embryogenic cells are cultured in a maintenance medium. The maintenance medium may be a solid medium, or it may be a liquid medium, which can be agitated to promote growth and multiplication of the embryogenic tissue. The osmolality of the maintenance medium is typically higher than the osmolality of the induction medium, typically in the range of about 180 to about 400 mM/kg. The maintenance medium may contain nutrients that sustain the embryogenic tissue, and may include hormones, such as one or more auxins and/or cytokinins, that promote cell division and growth of the embryogenic tissue. Typically, the concentrations of hormones in the maintenance medium is lower than their concentration in the induction medium.

It is generally desirable, though not essential, to include maltose as the sole, or principal, metabolizable sugar source in the maintenance medium. Examples of useful maltose concentrations are within the range of from about 1% to about 5%, such as about 3%. An example of a suitable maintenance medium is medium $BM_2$ set forth in EXAMPLE 1 herein. Pine embryogenic cells are typically cultured in, or on, a maintenance medium for a period of up to 6 months by weekly subculture, at a temperature of from 10° C. to 30° C., such as from 15° C. to 25° C., or such as from 20° C. to 23° C.

In the third step, embryogenic cells are cultured in, or on, a liquid development medium to produce cotyledonary somatic embryos, as described above. The embryogenic cells may first be rinsed in a rinse medium before they are cultured in, or on, a liquid development medium. The rinse medium typically has a similar composition to the liquid development medium, but includes a lower concentration of abscisic acid, and lacks the adsorbent composition and polyethylene glycol. An example of a suitable rinse medium is medium $BM_3$ set forth in EXAMPLE 1 herein.

In some embodiments, the methods further comprise the step of culturing the cotyledonary embryos in, or on, a stratification medium for a cold treatment prior to germination. Stratification (moist chilling) is a treatment used for overcoming germination resistance in the seeds of many temperate species (Taylor & Waring (1979) *Plant, Cell, And Environment* 2:165-171). The stratification medium may be a liquid medium, as described in EXAMPLES 2-5. Typically, the stratification medium is similar to development medium, but lacks abscisic acid, and typically does not include polyethylene glycol. The osmolality of the stratification medium is typically between about 100 and about 250 mM/kg, such as about 200 mM/kg. An exemplary stratification medium is $BM_6$ set forth in EXAMPLE 2. Typically, embryos form on the surface of a mass of embryogenic cells, such as an embryonal suspensor mass. The cotyledonary embryos may be separated into individual (singulated) cotyledonary embryos before culturing them in, or on, the stratification medium, or they may be cultured as a mass of unsingulated embryos. Embryos may be cultured in, or on, a stratification medium in a bioreactor, as described in EXAMPLE 5. Cotyledonary pine somatic embryos are typically cultured in, or on, a stratification medium in the dark for a period of from 1 weeks to 6 weeks, such as about 4 weeks, at a temperature of from 1° C. to 6° C., such as from 1° C. to 4° C.

In a second aspect, the methods comprise the step of culturing pine cotyledonary somatic embryos in, or on, a liquid stratification medium to produce stratified pine cotyledonary somatic embryos. Culturing pine cotyledonary somatic embryos in solid stratification medium has been shown to enhance the efficiency of germination of these embryos. However, solid or semi-solid stratification medium have the same disadvantages for large-scale production as those described for the solid or semi-solid development medium above. The second aspect of the present invention addresses these problems by culturing the cotyledonary somatic embryos in, or on, a liquid stratification medium. The composition of the liquid stratification used in the second aspect of the invention is as described above. An exemplary stratification medium is $BM_6$ set forth in EXAMPLE 2. Cotyledonary embryos may be cultured in liquid stratification medium or on liquid stratification medium-soaked pads. The cotyledonary embryos may be separated into individual (singulated) cotyledonary embryos before culturing them in, or on, the stratification medium, or they may be cultured as a mass of unsingulated embryos. Embryos may be cultured in, or on, a stratification medium in a bioreactor, as described in EXAMPLE 5. In some embodiments, at least about 100 cotyledonary embryos, such as about 1000 or about 10,000 of cotyledonary embryos, are cultured in a bioreactor. Typically, the cotyledonary embryos are cultured in, or on, a stratification medium for about 1 to about 6 weeks (such as about 4 weeks) at a temperature from about 1° C. and about 6° C. (such as from about 1° C. and about 4° C.), as described above.

In some embodiments, the methods of the second aspect of the invention comprise the steps of: (a) culturing pine somatic cells in, or on, an induction medium to produce embryogenic cells; (b) culturing the embryogenic cells prepared in step (a) in, or on, a maintenance medium to multiply the embryogenic cells; (c) culturing the embryogenic cells multiplied in step (b) in, or on, a development medium to produce cotyledonary somatic embryos; and (d) culturing the cotyledonary somatic embryos produced in step (c) in, or on, a liquid stratification medium to produce stratified cotyledonary somatic embryos.

In the first step, pine somatic cells are cultured in, or on, an induction medium to produce embryogenic cells, as described above. In the second step, the embryogenic cells are cultured in, or on, a maintenance medium to multiply the embryogenic cells, as described above. In the third step, the multiplied embryogenic cells are cultured in, or on, a development medium to produce cotyledonary embryos. The media and conditions used in the third step are as described above, except that the development medium may be a solid or semi-solid medium, as described in EXAMPLE 3. In the fourth step, the cotyledonary embryos are cultured in, or on, a liquid stratification medium to produce stratified cotyledonary somatic embryos, as described above.

After stratification, the cotyledonary embryos produced using the methods of the invention can optionally be germinated to form pine plants which can be grown into pine trees, if desired. Typically, cotyledonary embryos are subjected to a drying treatment before germination, as described in EXAMPLES 2-4. The cotyledonary embryos may also be disposed within manufactured seeds for subsequent germination. The cotyledonary embryos can be germinated, for example, on a solid germination medium, such as $BM_7$ medium set forth in EXAMPLE 2 herein. Typically, the cotyledonary somatic embryos are illuminated to stimulate germination. Typically, all the steps of the methods of the invention, except germination, are conducted in the dark. The germinated plants may be transferred to soil for further growth. For example, the germinated plants may be planted in soil in a greenhouse and allowed to grow before being transplanted to an outdoor site.

The methods of the first aspect of the invention produce a high yield of cotyledonary embryos of consistent quality. Thus, culturing embryogenic cells in, or on, a liquid development medium produces at least as high a yield and quality of cotyledonary embryos as culturing embryogenic cells in, or on, a solid or semi-solid development medium. In some embodiments, the methods of the invention produce a higher yield of somatic cotyledonary embryos than an identical method in which the embryogenic cells are cultured on a semi-solid development medium that is equivalent to the liquid development medium, as shown in EXAMPLE 1. Some of the media components may be varied to produce a solid development that is equivalent to the liquid development medium. For example, in a liquid medium abscisic acid is adsorbed more rapidly by the adsorbent composition than in a solid medium. Therefore, the concentration of abscisic acid in a liquid development medium may be higher than in an equivalent solid development medium to achieve the same effective concentration. Accordingly, the concentration of abscisic acid in a liquid development medium may be about twice as high as that in an equivalent solid development medium. Also, the concentrations of osmoticants, such as polyethylene glycol, may need to be elevated in a liquid medium to produce the same osmolality as that of the corresponding solid medium. Typically, a solid development medium that is equivalent to a liquid development medium has an osmolality that is within about 50 mM/kg of the osmolality of the liquid development medium. Some embodiments of the methods of the invention produce a yield of at least about 500 cotyledonary embryos, such as at least about 1000 cotyledonary embryos or at least about 2000 cotyledonary embryos, per 100 mg of embryogenic cells.

In some embodiments, the cotyledonary embryos produced using the methods of the invention develop faster and are longer than cotyledonary embryos produced using an otherwise identical method using an otherwise identical method that includes the use of a semi-solid development medium that is equivalent to the liquid development medium, as shown in EXAMPLE 4. In some embodiments of the methods of the invention that further comprise culturing the cotyledonary embryos in, or on, a liquid stratification medium, the yield of cotyledonary embryos and the germination efficiency are similar to (such as within about +/−10% or within about +/−20%) those obtained using an equivalent method without the use of liquid media in the development and stratification stages, as shown in EXAMPLE 4.

The methods of the second aspect of the invention produce an increased germination efficiency. Thus, the step of culturing pine cotyledonary somatic embryos in, or on, a liquid stratification medium may produce an increase, such as an about 2-fold to about 4-fold increase, in the germination efficiency of cotyledonary embryos compared to an equivalent method without the stratification step, as shown in EXAMPLE 2. In some embodiments, the use of a liquid stratification medium results in germination efficiencies that are similar (such as within about +/−10% or within about +/−20%) to those obtained by culturing the cotyledonary embryos on a semi-solid stratification medium that is otherwise identical to the liquid stratification medium, as shown in EXAMPLES 3 and 4.

The use of liquid development media and/or liquid stratification media according to the invention simplifies the production of cotyledonary embryos because liquid medium is easier to prepare, to store, and to use in automated production procedures. For example, the methods of the invention facilitates the production of cotyledonary embryos in bioreactors. In some embodiments of using bioreactors for the development and stratification stages, the methods provide yields of cotyledonary embryos and germination rates that are similar (such as within about +/−10% or within about +/−20%) to those obtained using small-scale cultures to the germination rate obtained without the use of a bioreactor but using an otherwise identical method, as described in EXAMPLE 5.

The methods of the invention can be used, for example, to produce clones of individual pine trees that possess one or more desirable characteristics, such as a rapid growth rate. Thus, in one aspect, the present invention provides methods for producing a population of genetically-identical pine somatic embryos. The term "genetically-identical pine somatic embryos" as used herein refers to embryos that are derived from the same original plant. The term includes pine somatic embryos containing a small number of mutations that may occur during the development of somatic embryos. The methods of this aspect of the invention each include the step of culturing embryogenic cells in a liquid development medium. Any of the methods described herein can be used to produce populations of genetically-identical cotyledonary somatic pine embryos.

The following examples merely illustrate the best mode now contemplated for practicing the invention, but should not be construed to limit the invention.

EXAMPLE 1

This Example shows a comparison of the yield and quality of Loblolly pine cotyledonary somatic embryos produced after culture on semi-solid development medium and after culture on a pad soaked in liquid development medium.

Methods: Four genotypes of Loblolly pine (*P. taeda*) (Geno A to Geno D) were used. Female gametophytes containing zygotic embryos were removed from seeds four to five weeks after fertilization. The seed coats were removed but the embryos were not further dissected out of the surrounding gametophyte other than to excise the nucellar end. The cones were stored at 4° C. until used. Immediately before removal of the immature embryos the seeds were sterilized utilizing an initial washing and detergent treatment followed by a ten minute sterilization in 15% $H_2O_2$. The explants were thoroughly washed with sterile distilled water after each treatment.

Table 1 sets forth the compositions of media useful for producing pine somatic embryos.

differs from the induction medium in that the concentrations of 2,4-D, BAP, and kinetin were reduced to 1.1 mg/L, 0.1 mg/L, and 0.1 mg/L, respectively. The temperature and photoperiod were again 22 to 25° C. with 24 hours in the dark.

ESMs were settled and rinsed of auxin and cytokinins in liquid $BM_3$ rinse medium before being transferred to a beaker for plating on solid development medium $BM_4$ or liquid development medium $BM_5$. The rinse and development media were similar to the maintenance medium but lacked growth hormones and instead contained abscisic acid (10 mg/l for the $BM_3$, 25 mg/l for $BM_4$, and 50 mg/l for $BM_5$) The development medium additionally contained an adsorbent composition (activated carbon, 1000 mg/l), and PEG 8000. The differences between the solid and the liquid development media used were that the concentrations of PEG 8000, maltose, and abscisic acid were higher in the liquid development

TABLE 1

Composition of Media for Loblolly Pine Embryogenic Culture

| Constituent | $BM_1$ (mg/L) | $BM_2$ (mg/L) | $BM_3$ (mg/L) | $BM_4$ (mg/L) | $BM_5$ (mg/L) |
|---|---|---|---|---|---|
| $NH_4NO_3$ | 150 | 150 | 150 | 150 | 150 |
| $KNO_3$ | 909.9 | 909.9 | 909.9 | 909.9 | 909.9 |
| $Ca(NO_3)_2 \cdot 4H_2O$ | 236.15 | 236.15 | 236.15 | 236.15 | 236.15 |
| $MgSO_4 \cdot 7H_2O$ | 246.5 | 246.5 | 246.5 | 246.5 | 246.5 |
| $Mg(NO_3)_2 \cdot 6H_2O$ | 256.5 | 256.5 | 256.5 | 256.5 | 256.5 |
| $MgCl_2 \cdot 6H_2O$ | 50 | 50 | 50 | 50 | 50 |
| $KH_2PO_4$ | 136 | 136 | 136 | 136 | 136 |
| $CaCl_2 \cdot 2H_2O$ | 50 | 50 | 50 | 50 | 50 |
| KI | 4.15 | 4.15 | 4.15 | 4.15 | 4.15 |
| $H_3BO_3$ | 15.5 | 15.5 | 15.5 | 15.5 | 15.5 |
| $MnSO_4 \cdot H_2O$ | 10.5 | 10.5 | 10.5 | 10.5 | 10.5 |
| $ZnSO_4 \cdot 7H_2O$ | 14.4 | 14.4 | 14.4 | 14.4 | 14.4 |
| $Na_2MoO_4 \cdot 2H_2O$ | 0.125 | 0.125 | 0.125 | 0.125 | 0.125 |
| $CuSO_4 \cdot 5H_2O$ | 0.125 | 0.125 | 0.125 | 0.125 | 0.125 |
| $CoCl_2 \cdot 6H_2O$ | 0.125 | 0.125 | 0.125 | 0.125 | 0.125 |
| $FeSO_4 \cdot 7H_2O$ | 27.87 | 27.87 | 27.87 | 13.93 | 13.93 |
| $Na_2EDTA$ | 37.26 | 37.26 | 37.26 | 18.63 | 18.63 |
| Nicotinic acid | 0.5 | 0.5 | 0.5 | 0.5 | 0.5 |
| Pyridoxine•HCl | 0.5 | 0.5 | 0.5 | 0.5 | 0.5 |
| Thiamine•HCl | 1 | 1 | 1 | 1 | 1 |
| Glycine | 2 | 2 | 2 | 2 | 2 |
| L-Proline | | | 100 | 100 | 100 |
| L-Asparagine | | | 100 | 100 | 100 |
| L-Arginine | | | 50 | 50 | 50 |
| L-Alanine | | | 20 | 20 | 20 |
| L-Serine | | | 20 | 20 | 20 |
| PEG 8000 | | | | 130000 | 180000 |
| Myo-Inositol | 200 | 200 | 1000 | 1000 | 1000 |
| Casein hydrolysate | 500 | 500 | 500 | 500 | 500 |
| L-Glutamine | 1000 | 1000 | 1000 | 1000 | 1000 |
| Maltose | 30000 | 30000 | 25000 | 20000 | 25000 |
| GELRITE | 1600 | | | 2500 | |
| Activated carbon | | | | 1000 | 1000 |
| Abscisic acid | | | 10 | 25 | 50 |
| 2,4-D | 3.3 | 1.1 | | | |
| BAP | 0.4 | 0.1 | | | |
| Kinetin | 0.4 | 0.1 | | | | pH adjusted to 5.7

Sterile gametophytes with intact embryos were placed on solid $BM_1$ culture medium and held in an environment at 22° C. to 25° C. with a 24 hour dark photoperiod for a time of 3 to 5 weeks. The length of time depends on the particular genotype being cultured. At the end of this time a white mucilaginous mass (embryonal suspensor mass, ESM) formed in association with the original explants. Microscopic examination typically revealed numerous early stage embryos associated with the mass.

ESMs generated in the induction stage were placed on liquid $BM_2$ maintenance and multiplication medium. This medium than in the solid development medium, and that the solid development medium additionally contained 2500 mg/l gellan gum.

For solid plates, 1 ml of settled ESMs (about 100 mg fresh weight) were plated onto filter paper on a blotter, and the filters transferred to solid $BM_4$ media when the ESMs were drained. For liquid-pad plates, 1 ml of settled ESMs were directly transferred to filter papers on top of $BM_5$ medium-soaked pads and excess liquid was aspirated. 10 plates were used for each genotype on each development medium. Development was carried out in complete darkness at a temperature of 22°-25° C. until elongated cotyledonary embryos developed (typically 10 to 12 weeks).

Results: Observations on embryo quality were made at 4, 8, and 10 weeks after plating. Quality assessments included color, size, and shape of the embryos, as well as the condition of the underlying ESMs. After 4 weeks, the solid $BM_4$ plates appeared more wet at the surface than the liquid $BM_5$ plates, and the ESMs in the liquid $BM_5$ plates was proliferating and forming more, albeit smaller, embryos. Geno A had more cotyledonary embryos than the other genotypes. By the 8th week, all genotypes were producing cotyledonary embryos on both liquid and solid development media. However, the liquid cultures also showed many smaller embryos at earlier developmental stages. After 10 weeks, embryo quality was similar as at 8 weeks, but all embryos were a little further developed. Geno A was the most developed, with embryos on solid $BM_4$ media being very green and flexing at the cotyledons, followed by genotype B. Geno C and Geno D on liquid $BM_5$ development medium lagged behind.

Yield was assessed by counting cotyledonary embryos through the plate lids at 10 weeks. The average yields of cotyledonary embryos produced on liquid $BM_5$ or on solid $BM_4$ development medium for all genotypes considered together is shown in Table 2. The liquid $BM_5$ development medium resulted in a significantly higher yield compared to the solid $BM_4$ development medium.

TABLE 2

Average Cotyledonary Embryo Yields

| Development medium | Average quadrant yield (standard error) | Average whole plate yield (standard error) | p-value ranking |
|---|---|---|---|
| $BM_4$ (solid) | 10.3 (1.56) | 41 (6.22) | A |
| $BM_5$ (liquid) | 60.2 (7.35) | 241 (29.42) | B |

Genotypic differences were observed both in absolute yield and the difference in yield using solid or liquid development medium, as shown in Table 3.

TABLE 3

Cotyledonary Embryo Yields for Each Genotypes

| Development medium | Geno A (standard error) | Geno B (standard error) | Geno C (standard error) | Geno D (standard error) |
|---|---|---|---|---|
| $BM_4$ (solid) | 104 (7.7) | 31 (3.3) | 21 (2.8) | 19 (2.9) |
| $BM_5$ (liquid) | 479 (48.2) | 306 (48.9) | 84 (14.0) | 149 (11.5) |

These results show that for all four genotypes, the yield of cotyledonary increased substantially using the liquid pad development system compared to solid development medium, without negatively affecting the quality of the embryos.

EXAMPLE 2

This Example shows a comparison of the germination rate of cotyledonary somatic embryos from Loblolly pine with and without culture on liquid stratification medium-soaked pads.

Methods: Seven genotypes of Loblolly pine (Geno E to Geno K) were used. The induction, maintenance/multiplication, and development stages were as described in EXAMPLE 1. For the development stage, liquid development medium $BM_5$ was used (see Table 1).

After 10 to 12 weeks of development, one group of cotyledonary embryos of each genotype were cultured on liquid stratification medium $BM_6$ (Table 4) and cultured for 4 weeks at about 4° C. before being transferred to petri dishes over $K_2SO_4$ (97% humidity) for 3 weeks in the dark at room temperature (drying treatment). The other group was subjected to the drying treatment directly after the development stage. After the drying treatment, cotyledonary embryos from both groups were imbibed on liquid $BM_7$ medium (Table 4, without TC agar) for at least 4 hours before being transferred individually onto solid $BM_7$ medium (Table 4) and light for germination.

TABLE 4

Composition of Media for Loblolly Pine Embryo Culture

| Constituent | $BM_6$ (mg/l) | $BM_7$ (mg/l) | $BM_8$ (mg/l) |
|---|---|---|---|
| $NH_4NO_3$ | 150 | 206.25 | 150 |
| $KNO_3$ | 909.9 | 1170 | 909.9 |
| $Ca(NO_3)_2 \cdot 4H_2O$ | 236.15 | | 236.15 |
| $MgSO_4 \cdot 7H_2O$ | 246.5 | 185 | 246.5 |
| $Mg(NO_3)_2 \cdot 6H_2O$ | 256.5 | | 256.5 |
| $MgCl_2 \cdot 6H_2O$ | 50 | | 50 |
| $KH_2PO_4$ | 136 | 85 | 136 |
| $CaCl_2 \cdot 2H_2O$ | 50 | 220 | 50 |
| KI | 4.15 | 0.415 | 4.15 |
| $H_3BO_3$ | 15.5 | 3.1 | 15.5 |
| $MnSO_4 \cdot H_2O$ | 10.5 | 8.45 | 10.5 |
| $ZnSO_4 \cdot 7H_2O$ | 14.4 | 4.3 | 14.4 |
| $Na_2MoO_4 \cdot 2H_2O$ | 0.125 | 0.125 | 0.125 |
| $CuSO_4 \cdot 5H_2O$ | 0.125 | 0.0125 | 0.125 |
| $CoCl_2 \cdot 6H_2O$ | 0.125 | 0.0125 | 0.125 |
| $FeSO_4 \cdot 7H_2O$ | 13.93 | 13.93 | 27.87 |
| $Na_2EDTA$ | 18.63 | 18.63 | 37.26 |
| Nicotinic acid | 0.5 | 0.5 | 0.5 |
| Pyridoxine•HCl | 0.5 | 0.5 | 0.5 |
| Thiamine•HCl | 1 | 1 | 1 |
| Glycine | 2 | 2 | 2 |
| L-Proline | 100 | | 100 |
| L-Asparagine | 100 | | 100 |
| L-Arginine | 50 | | 50 |
| L-Alanine | 20 | | 20 |
| L-Serine | 20 | | 20 |
| PEG 8000 | | | 120000 |
| Myo-Inositol | 1000 | 100 | 1000 |
| Casein hydrolysate | 500 | | 500 |
| L-Glutamine | 1000 | | 1000 |
| Sucrose | | 20000 | |
| Maltose | 25000 | | 25000 |
| Glucose | | | 10000 |
| GELRITE | | | |
| TC Agar | | 8000 | |
| Activated carbon | 1000 | 2500 | 1000 |
| Abscisic acid | | | 25 | pH adjusted to 5.7

Results: Germination was assessed after 8 to 10 weeks in the light by observing the number of embryos with epicotyls, the number of embryos with straight hypocotyls, the number of embryos with roots, and the number of embryos with both epicotyl and roots (germinants). Since the data came from many experiments, 54 groups were created with each group consisting of plates from the same genotype and varying only in whether or not they had been subjected to a stratification treatment. The germination results for all the genotypes individually show that the liquid stratification treatment resulted in statistically significant increases in the percentage of embryos with epicotyls, the percentage of embryos with straight hypocotyls, the percentage of embryos with roots, and the percentage of embryos with both epicotyls and roots (germination efficiency), as shown in Table 5. For example, the liquid stratification treatment resulted in at least about 4-fold increases in germination efficiencies for Geno F. For all genotypes combined, the stratification treatment produced statistically significant (p<0.05) increases in the percentage of embryos with epicotyls, the percentage of embryos with straight hypocotyls, the percentage of embryos with roots, and the percentage of embryos with both epicotyls and roots.

germination frequencies were observed between embryos stratified on semi-solid stratification medium and embryos stratified on liquid stratification medium. The combined germination frequencies were 11.8% after stratification on liquid medium and 10.2% after stratification on semi-solid medium for Geno M, Geno N, and Geno O. No bipolar germinants

TABLE 5

Germination Results With and Without Liquid Stratification Treatment

| Genotype | Stratification | Embryos with Epicotyls (%) | Embryos with straight Hypocotyls (%) | Embryos with Roots (%) | Embryos with both Epicotyls and Roots (%) |
|---|---|---|---|---|---|
| Geno E | No | 18 | 1 | 9 | 2 |
|  | Yes | 58 | 6 | 10 | 4 |
|  | Std error | 7.03 | 1.35 | 2.37 | 1.22 |
|  | p value | 0.0032 | 0.0183 | 0.8057 | 0.5026 |
| Geno F | No | 40 | 7 | 7 | 3 |
|  | Yes | 62 | 24 | 18 | 13 |
|  | Std error | 3.32 | 2.03 | 2.10 | 1.52 |
|  | p value | 0.0001 | 0.0001 | 0.0008 | 0.0001 |
| Geno G | No | 23 | 0 | 2 | 0 |
|  | Yes | 21 | 1 | 0 | 0 |
|  | Std error | 6.93 | 0.45 | 0.95 | — |
|  | p value | 0.8657 | 0.3632 | 0.1801 | — |
| Geno H | No | 14 | 0 | 26 | 4 |
|  | Yes | 24 | 2 | 38 | 11 |
|  | Std error | 3.78 | 1.02 | 0.81 | 1.55 |
|  | p value | 0.1921 | 0.4226 | 0.0088 | 0.096 |
| Geno I | No | 26 | 2 | 28 | 5 |
|  | Yes | 17 | 13 | 51 | 11 |
|  | Std error | 10.43 | 1.35 | 0.50 | 2.31 |
|  | p value | 0.6231 | 0.0336 | 0.0009 | 0.2499 |
| Geno J | No | 13 | 0 | 16 | 0 |
|  | Yes | 62 | 0 | 52 | 45 |
|  | Std error | — | — | — | — |
|  | p value | — | — | — | — |
| Geno K | No | 8 | 0 | 34 | 5 |
|  | Yes | 0 | 0 | 52 | 0 |
|  | Std error | — | — | — | — |
|  | p value | — | — | — | — |

EXAMPLE 3

This Example shows a comparison of the germination rate of cotyledonary somatic embryos from Loblolly pine cultured on liquid stratification medium-soaked pads and on semi-solid stratification medium.

Methods: Four genotypes of Loblolly pine (Geno L to Geno O) were used. The induction and maintenance/multiplication, and development stages were as described in EXAMPLE 1. The composition of the development medium used was as described for $BM_4$ (see Table 1), except that the concentrations of $FeSO_4.7H_2O$ and $Na_2EDTA$ were 2-fold higher. 20 plates were used for each genotype and 1.5 ml of settled ESMs (about 150 mg fresh weight) were plated onto filter papers in each plate.

After 10 to 12 weeks of development, 10 plates of cotyledonary embryos of each genotype were cultured on liquid stratification medium $BM_6$ (Table 4) and 10 plates of cotyledonary embryos of each genotype were cultured on a semi-solid stratification medium ($BM_6$+2500 mg/l gelrite). All plates cultured for 4 weeks at about 4° C. After stratification, embryos were dried for three weeks in small petri plates on mesh bridges suspended over water in magenta boxes, after which the filter papers were moved to pads soaked in liquid $BM_7$ medium (Table 4, without TC agar) for about 24 hours before being transferred onto solid $BM_7$ medium (Table 4) and light for germination.

Results: The germination frequencies were lower than usually observed for these genotypes. However, no differences in germination frequencies were observed between embryos stratified on semi-solid stratification medium and embryos stratified on liquid stratification medium. The combined germination frequencies were 11.8% after stratification on liquid medium and 10.2% after stratification on semi-solid medium for Geno M, Geno N, and Geno O. No bipolar germinants were observed for Geno L using either semi-solid or liquid stratification medium. However, the percentage of embryos that developed epicotyls was similar (14.8% using liquid stratification medium and 14.6% using semi-solid stratification medium).

EXAMPLE 4

This Example describes an exemplary method of the invention for producing cotyledonary somatic embryos from Loblolly pine using pads soaked in liquid development and liquid stratification media.

Methods: Three genotypes of Loblolly pine (Geno P to Geno R) were used. The induction and maintenance/multiplication stages were as described in EXAMPLE 1. For each genotype, 0.5 ml of settled ESMs (about 50 mg fresh weight) were transferred onto each of six pads soaked with liquid development medium $BM_8$ in plates (see Table 4). The plates were allowed to develop in the dark for 12 weeks and assessed for yield and quality (size, shape, color, and length) of cotyledonary embryos. Cotyledonary embryos on all plates were counted to determine the yield. One plate of each genotype was randomly selected for measurement of embryo lengths using the ocular micrometer on the microscopes. The lengths for the longest 20 embryos per plate were averaged.

Cotyledonary embryos were singulated to filter papers on pads soaked with liquid stratification medium $BM_6$ (see Table 4) and incubated at 0° C. to 4° C. for 4 weeks. After the cold treatment, the filter papers with embryos were transferred to an empty plate suspended over water on a mesh bridge in a magenta box and incubated for 3 weeks in the dark at room temperature. This allowed partial drying of embryos at 97-99% humidity. Following the treatment over water, the filter paper with embryos was placed on a pad soaked with liquid germination medium ($BM_7$ without the agar, see Table 4) for 24 hours. The embryos were subsequently transferred to semi-solid germination medium $BM_7$, allowed to elongate in the dark for 7 days, after which the embryos were moved to the light to allow germination over the next 11 weeks.

Results: For all genotypes, the cotyledonary embryos cultured on the liquid development medium-soaked pads developed about 3 weeks earlier (at 9 weeks) than embryos of the same genotypes cultured on semi-solid development medium. After 12 weeks of development, the hypocotyls were longer and better delineated, and the cotyledons were larger and more numbers than is observed for embryos cultured on semi-solid development media. The average lengths of the 20 longest embryos were 3.1 mm (standard deviation 0.17; standard error 0.04) for Geno P, 3.5 mm (standard deviation 0.24; standard error 0.05) for Geno Q, and 3.5 mm (standard deviation 0.42; standard error 0.09) for Geno R. Embryo lengths above 3 mm were rarely seen in for embryos cultured on solid or semi-solid development media.

The yield of cotyledonary embryos after 12 weeks of development is shown in Table 6. The yields and germination percentages are within or above the normal ranges for these genotypes cultured on an equivalent semi-solid development or an identical semi-solid stratification media.

TABLE 6

Yield of Cotyledonary Embryos and Germinants

|  | Geno P | Geno Q | Geno R | All Genotypes |
|---|---|---|---|---|
| Yield of embryos per ml of settled ESMs | 20 | 95 | 64 | 60 |
| Percent germination | 33 | 50 | 34 | 39 |
| Average yield of germinants per ml of settled ESMs | 7 | 47 | 22 | 23 |

EXAMPLE 5

This Example describes an exemplary method of the invention for the large-scale production of cotyledonary somatic embryos from Loblolly pine using a liquid pad system in bioreactors.

Methods: Two genotypes of Loblolly pine (Geno S and Geno T), were used. Induction of ESMs and the maintenance/multiplication stage was as described in EXAMPLE 1. Two bioreactors were used for culturing the ESMs using liquid development medium $BM_8$ (see Table 4). For Geno S, a stainless steel tray containing 64 cellulose pads (2"×2") was used. About 1600 ml of liquid development medium was pipetted evenly over all pads, so that excess medium pooled in the bottom of the tray. For Geno T, a plastic Cambro tray containing two layers of two large cellulose pads cut to fit half the pan (~8"×8") were used. Liquid development medium (~1600 ml) was poured at the sides of the pads to allow the pads to soak up medium from the bottom.

Large size Whatman #4 filter papers were added on top of the media-soaked pads in both bioreactor trays. After rinsing the ESMs in $BM_3$ medium (see Table 1), ESMs in a 2:1 ratio with $BM_3$ were transferred onto the filter papers with a 5-ml pipette. 3 ml of Geno S ESMs (about 300 mg fresh weight) of were plated onto each of 16 filter papers that rested on four pads (about 4.8 g of ESMs in bioreactor). 5 ml of Geno T ESMs (about 500 mg fresh weight) were plated onto each of 2 filter papers (about 1 g of ESMs in bioreactor). The lids of the bioreactors were secured with binder clips on each side.

After 12 weeks of development, the filter papers with the ESMs and embryos were transferred to large Cambro pans containing two pads cut to fit half of the pan and saturated with a liquid stratification medium $BM_6$ (Table 4) and cultured for 4 weeks in the dark at about 4° C.

After stratification, cotyledonary embryos of Geno S, and cotyledonary embryos of Geno T were transferred to dry filter papers in small petri plates. The dry filter papers were then transferred to petri dishes over $K_2SO_4$ (97% humidity) for 3 weeks in the dark at room temperature. After this drying treatment, the embryos were imbibed on liquid $BM_7$ medium (Table 4, without TC agar) for at least 4 hours before being transferred individually onto solid $BM_7$ medium (Table 4) for germination.

Results: Development of cotyledonary embryos was successful using both bioreactor types and both types of pads. The yield of cotyledonary embryos cultured in bioreactors was similar to the yield obtained using small-scale cultures. The germination frequencies were similar to germination frequencies obtained without using bioreactors, i.e., between about 56% and about 73% for Geno S, and between about 26% and about 30% for Geno T. The germination frequencies show that the use of liquid development and stratification media in bioreactors produced yields of cotyledonary embryos and germinants comparable to the yields obtained without the use of bioreactors. However, the use of bioreactors was considerably less labor-intensive and the embryos developed. faster in bioreactors.

EXAMPLE 6

This Example describes an exemplary method of the invention for producing cotyledonary somatic embryos from Loblolly pine (*Pinus taeda*) in liquid development medium.

Methods: Two genotypes of Loblolly pine (*P. taeda*) (Geno U and Geno V) were used. Induction of ESMs and the maintenance/multiplication stage was as described in EXAMPLE 1.

TABLE 7

Composition of Media for Loblolly Pine Embryo Culture

| Constituent | $BM_9$ (mg/l) | $BM_{10}$ (mg/l) |
|---|---|---|
| $NH_4NO_3$ | 150 | 150 |
| $KNO_3$ | 909.9 | 909.9 |
| $Ca(NO_3)_2 \cdot 4H_2O$ | 236.15 | 236.15 |
| $MgSO_4 \cdot 7H_2O$ | 246.5 | 246.5 |
| $Mg(NO_3)_2 \cdot 6H_2O$ | 256.5 | 256.5 |
| $MgCl_2 \cdot 6H_2O$ | 50 | 50 |
| $KH_2PO_4$ | 136 | 136 |
| $CaCl_2 \cdot 2H_2O$ | 50 | 50 |
| KI | 4.15 | 4.15 |
| $H_3BO_3$ | 15.5 | 15.5 |
| $MnSO_4 \cdot H_2O$ | 10.5 | 10.5 |
| $ZnSO_4 \cdot 7H_2O$ | 14.4 | 14.4 |
| $Na_2MoO_4 \cdot 2H_2O$ | 0.125 | 0.125 |
| $CuSO_4 \cdot 5H_2O$ | 0.125 | 0.125 |
| $CoCl_2 \cdot 6H_2O$ | 0.125 | 0.125 |
| $FeSO_4 \cdot 7H_2O$ | 27.87 | 13.93 |
| $Na_2EDTA$ | 37.26 | 18.63 |
| Nicotinic acid | 0.5 | 0.5 |
| Pyridoxine•HCl | 0.5 | 0.5 |
| Thiamine•HCl | 1 | 1 |

TABLE 7-continued

Composition of Media for Loblolly Pine Embryo Culture

| Constituent | $BM_9$ (mg/l) | $BM_{10}$ (mg/l) |
|---|---|---|
| Glycine | 2 | 2 |
| Myo-Inositol | 200 | 200 |
| Casein hydrolysate | 500 | 500 |
| L-Glutamine | 1000 | |
| Maltose | 30000 | 30 |
| Glucose | | |
| Activated carbon | | 200 |
| GA4/7 | | 10 |
| Abscisic acid | 1 | 10 |
| 2,4-D | 1.1 | |
| BAP | 0.1 | |
| Kinetin | 0.1 | | pH adjusted to 5.7

ESMs of both genotypes were diluted at a 1:5 ratio of ESMs to medium into a flask containing either liquid development medium $BM_9$ or $BM_{10}$ (see Table 7). $BM_9$ contained abscisic acid, 2,4-D, BAP, and kinesin. $BM_{10}$ contained abscisic acid, GA4/7, and charcoal. The osmolality of $BM_9$ and $BM_{10}$ was 200 mM/kg. Flasks were shaken at 90 r.p.m. on a rotatory shaker. Each flask was subcultured every week into fresh development medium.

Results: After the third week, both genotypes had produced cotyledonary stage embryos in liquid development medium $BM_{10}$: Geno U produced about 60 cotyledonary embryos per 100 mg of ESMs and Geno V produced about 40 cotyledonary embryos per 100 mg of ESMs.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for producing stratified cotyledonary pine somatic embryos, comprising:
   (a) culturing pine embryogenic cells in, or on, a maintenance medium to multiply the pine embryogenic cells;
   (b) culturing the pine embryogenic cells multiplied in step (a) in, or on, a liquid development medium comprising abscisic acid and polyethylene glycol to produce cotyledonary pine somatic embryos; and
   (c) culturing the cotyledonary pine somatic embryos produced according to step (b) in, or on, a liquid stratification medium to produce stratified cotyledonary pine somatic embryos, wherein the liquid stratification medium has an osmolality between about 100 mM/kg and about 250 mM/kg.

2. The method of claim 1, wherein at least about 1000 mg of embryogenic cells produced in step (a) are cultured in, or on, the liquid development medium.

3. The method of claim 1, wherein the embryogenic cells produced in step (a) are cultured on pads soaked in liquid development medium.

4. The method of claim 1, wherein the embryogenic cells produced in step (a) are cultured in liquid development medium.

5. The method of claim 1, wherein the liquid development medium has an osmolality between about 200 mM/kg to about 500 mM/kg.

6. The method of claim 1, wherein the yield is at least between about 1000 and about 2000 cotyledonary pine somatic embryos per 100 mg of embryogenic cells produced in step (a).

7. The method of claim 1, wherein the pine is Loblolly pine.

8. The method of claim 1, wherein the pine embryogenic cells are cultured in, or on, a liquid development medium in a bioreactor.

9. The method of claim 8, wherein the yield of cotyledonary pine somatic embryos is similar to the yield obtained using an identical method but without the use of a bioreactor.

10. The method of claim 1, wherein the cotyledonary pine somatic embryos are cultured in, or on, a liquid stratification medium for about 2 to about 12 weeks at a temperature between about 0° C. and about 10° C.

11. The method of claim 1, wherein the cotyledonary pine somatic embryos are cultured in, or on, a liquid stratification medium in a bioreactor.

12. The method of claim 11, wherein the germination rate of the stratified cotyledonary pine somatic embryos is similar to the germination rate obtained using an identical method but without the use of a bioreactor.

13. The method of claim 1, wherein between about 100 and about 1000 cotyledonary pine somatic embryos produced in step (b) are cultured in, or on, a liquid stratification medium.

14. The method of claim 1, wherein the cotyledonary pine somatic embryos are cultured on pads soaked in liquid stratification medium.

15. The method of claim 1, wherein the cotyledonary pine somatic embryos are cultured in liquid stratification medium.

16. The method of claim 1, wherein the cotyledonary pine somatic embryos are cultured in, or on, the liquid stratification medium for about 1 to about 6 weeks at a temperature between about 0° C. and about 6° C.

17. The method of claim 1, wherein the germination rate of the stratified cotyledonary pine somatic embryos is similar to the germination rate of stratified cotyledonary pine somatic embryos produced using an otherwise identical method but using a semi-solid stratification medium that is identical to the liquid stratification medium.

18. The method of claim 1, wherein the liquid stratification medium does not contain abscisic acid.

19. The method of claim 1, wherein the liquid development medium further comprises an adsorbent composition.

20. The method of claim 19, wherein the adsorbent composition is charcoal.

* * * * *